United States Patent [19]

Kanekiyo et al.

[11] Patent Number: 5,000,877
[45] Date of Patent: Mar. 19, 1991

[54] AQUEOUS LIQUID DETERGENT CONTAINING AN N-ACYLASPARTATE AND A BETAINE OR IMIDAZOLINE SURFACTANT

[75] Inventors: Takazumi Kanekiyo; Noriaki Tanaka; Suzuo Sano, all of Mie, Japan

[73] Assignee: Mitsubishi Petrochemical Co., Ltd., Tokyo, Japan

[21] Appl. No.: 390,211

[22] Filed: Aug. 7, 1989

[30] Foreign Application Priority Data

Aug. 12, 1988 [JP] Japan .................................. 63-201513
Sep. 28, 1988 [JP] Japan .................................. 63-242955

[51] Int. Cl.$^5$ .................... C11D 1/10; C11D 1/88; C11D 1/90; C11D 17/08
[52] U.S. Cl. .................................... 252/542; 252/153; 252/173; 252/544; 252/546; 252/DIG. 5; 252/DIG. 7
[58] Field of Search .............. 252/173, 524, 527, 542, 252/546, DIG. 5, DIG. 7, DIG. 13, DIG. 14; 424/70

[56] References Cited

U.S. PATENT DOCUMENTS

| | | | |
|---|---|---|---|
| 3,663,459 | 5/1972 | Yoshida | 252/546 |
| 3,707,505 | 12/1972 | Maeda | 252/136 |
| 4,273,684 | 6/1981 | Nagashima | 252/544 |
| 4,555,360 | 11/1985 | Bissett | 252/546 |
| 4,578,216 | 3/1986 | Fujii | 252/542 |
| 4,595,526 | 6/1986 | Lai | 252/545 |
| 4,749,515 | 6/1988 | Miyamoto | 252/545 |
| 4,772,424 | 9/1988 | Greeb | 252/546 |
| 4,885,107 | 12/1989 | Wetzel | 252/106 |

FOREIGN PATENT DOCUMENTS

| | | |
|---|---|---|
| 0150323 | 8/1985 | European Pat. Off. |
| 3637683 | 5/1987 | Fed. Rep. of Germany |
| 2074498 | 10/1971 | France |
| 2457891 | 12/1980 | France |
| 48-10921 | 4/1973 | Japan ................. 252/546 |
| 48-33964 | 10/1973 | Japan ................. 252/546 |
| 50-23682 | 8/1975 | Japan |
| 51-42603 | 11/1976 | Japan |
| 53-46841 | 12/1978 | Japan ................. 252/546 |
| 54-160405 | 12/1979 | Japan ................. 252/546 |
| 56-76500 | 6/1981 | Japan |
| 59-138298 | 8/1984 | Japan ................. 252/546 |
| 61-291700 | 12/1986 | Japan ................. 252/546 |

Primary Examiner—Dennis Albrecht
Attorney, Agent, or Firm—Oblon, Spivak, McClelland, Maier & Neustadt

[57] ABSTRACT

A liquid detergent composition is disclosed, which contains an N-acylaspartic acid or a salt thereof represented by formula (I):

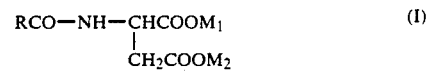

wherein R represents an alkyl or alkenyl group having from 7 to 21 carbon atoms; and $M_1$ and $M_2$ each represents a hydrogen atom or a cation derived from Na, K, $NH_4$ or an alkanolamine, and a nitrogen-containing surface active agent selected from the group consisting of an alkylbetaine or alkylamidebetaine represented by formula (II):

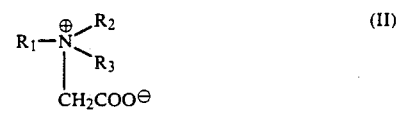

wherein $R_1$ represents and alkyl or alkenyl group having from 10 to 22 carbon atoms which may contain an amide linkage in the chain thereof; and $R_2$ and $R_3$ each represents an alkyl group having from 1 to 3 carbon atoms, and an imidazoline compound represented by formula (III):

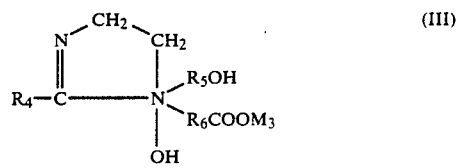

wherein $R_4$ represents an alkyl or alkenyl group having from 4 to 18 carbon atoms; $R_5$ represents an alkylene group having from 1 to 4 carbon atoms; $R_6$ represents an alkylene group having from 1 to 4 carbon atoms or a hydroxyl-substituted alkylene group having from 1 to 4 carbon atoms; and $M_3$ represents a hydrogen atom or a cation derived from Na, K, $NH_4$ or an alkanolamine. The composition exhibits excellent detergency and foamability while being mild to the skin.

2 Claims, No Drawings

AQUEOUS LIQUID DETERGENT CONTAINING AN N-ACYLASPARTATE AND A BETAINE OR IMIDAZOLINE SURFACTANT

FIELD OF THE INVENTION

This invention relates to a novel liquid detergent composition. More particularly, it relates to a liquid detergent composition useful as hair shampoo, body shampoo, liquid face soap, and dishwashing detergent.

BACKGROUND OF THE INVENTION

Anionic surface active agents, such as alkyl benzenesulfonates, higher alcohol sulfates, alkyl ether sulfates, and higher fatty acid salts, have widely been used in detergents, such as shampoo. The detergents containing these surface active agents are unsatisfactory in mildness to the skin. On the other hand, there is now a tendency that an N-acylglutamic acid salt obtained by subjecting one of amino acids, glutamic acid to acylation is incorporated into hair shampoo or body shampoo not only because of its mildness to the skin but because of its inhibitory effect on growth of harmful microorganisms causing skin diseases.

However, an aqueous solution of the N-acylglutamate per se lacks detergency and foamability for cleaning off extremely oily dirt, for example, hair applied with pomade.

It has been proposed to use the N-acylglutamate in combination with an alkyl betaine or imidazoline surface active agent to thereby improve detergency and foamability without impairing mildness to the skin as disclosed in JP-B-50-23682 and JP-B-51-42603 (the term "JP-B" as used herein means an "examined Japanese patent publication"), but these detergents are still unsatisfactory in detergency and foamability.

SUMMARY OF THE INVENTION

One object of this invention is to provide a liquid detergent composition exhibiting excellent foamability, detergency and low-temperature stability while retaining mildness to the skin.

That is, the present invention relates to a detergent composition containing an N-acylaspartic acid or a salt thereof represented by formula (I):

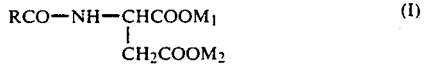

wherein R represents an alkyl or alkenyl group having from 7 to 21 carbon atoms; and $M_1$ and $M_2$ each represents a hydrogen atom or a cation derived from Na, K, $NH_4$ or an alkanolamine, and a nitrogen-containing surface active agent selected from the group consisting of an alkylbetaine or alkylamidobetaine represented by formula (II):

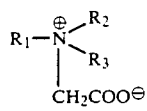

wherein $R_1$ represents an alkyl or alkenyl group having from 10 to 22 carbon atoms which may contain an amide linkage in the chain thereof; and $R_2$ and $R_3$ each represents an alkyl group having from 1 to 3 carbon atoms, and an imidazoline compound represented by formula (III):

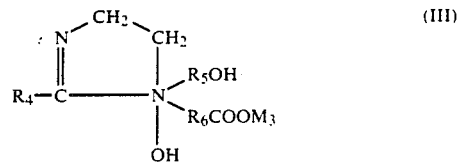

wherein $R_4$ represents an alkyl or alkenyl group having from 4 to 18 carbon atoms; $R_5$ represents an alkylene group having from 1 to 4 carbon atoms; $R_6$ represents an alkylene group having from 1 to 4 carbon atoms or a hydroxyl-substituted alkylene group having from 1 to 4 carbon atoms; and $M_3$ represents a hydrogen atom or a cation derived from Na, K, $NH_4$ or an alkanolamine.

DETAILED DESCRIPTION OF THE INVENTION

The N-acylaspartic acid or a salt thereof represented by formula (I) which can be used in the detergent composition of the present invention includes an L-form, a D-form, and a mixture thereof. It can be synthesized, for example, by reacting aspartic acid and a fatty acid halide having from 8 to 22 carbon atoms in the presence of a basic catalyst.

Specific examples of the N-acylaspartic acid or a salt thereof which can be used suitably are N-lauroylaspartic acid, N-myristoylaspartic acid, N-palmitoylaspartic acid, N-stearoylaspartic acid, N-palmitoylaspartic acid, N-oleoylaspartic acid, and N-cocoylaspartic acid, and their salts, e.g., sodium salts, potassium salts, monoethanolammonium salts, diethanolammonium salts, and triethanolammonium salts.

The nitrogen-containing surface active agent which can be used in the detergent composition of the present invention can be selected from alkylbetaines and alkylamidobetaines represented by formula (II) and imidazoline compounds represented by formula (III).

The compounds of formula (II) can be obtained by reacting a tertiary amine whose nitrogen atom having an alkyl or alkenyl group containing from 10 to 22 carbon atoms which may contain an amide linkage in the chain thereof and two alkyl groups containing from 1 to 3 carbon atoms with a monohalogenated acetic acid salt. For example, lauryldimethylaminoacetic acid betaine can be synthesized by heating a mixture of lauryldimethylamine and sodium monochloroacetate.

Specific examples of the compounds formula (II) include alkylbetaines having an alkyl group containing from 10 to 18 carbon atoms as the moiety $R_1$, e.g., lauryldimethylaminoacetic acid betaine, myristyldimethylaminoacetic acid betaine, stearyldimethylaminoacetic acid betaine, oleyldimethylaminoacetic acid betaine, laurylmethylethylaminoacetic acid betaine, and laurylmethyl-n-propylaminoacetic acid betaine; and alkylamidobetaines containing from 10 to 22 carbon atoms and having an amide linkage in the chain thereof, e.g., lauramidopropyldimethylaminoacetic acid betaine, myristamidopropyldimethylaminoacetic acid betaine, stearamidopropyldimethylaminoacetic acid betaine, oleamidopropyldimethylaminoacetic acid betaine, palmitamidopropyldimethylaminoacetic acid betaine, coconut oil fatty acid amidopropyldimethylaminoacetic acid betaine, lauramidopropylmethylethylaminoacetic acid betaine, lauramido-propylmethyl-n-propylaminoacetic acid betaine, lauramidoethyldimethylaminoacetic acid betaine, and lauramidobutyldimethylaminoacetic acid betaine.

The compounds of formula (III) can be prepared by reacting a long-chain fatty acid having from 5 to 19 carbon atoms with a β-hydroxyalkylethylenediamine containing from 1 to 4 carbon atoms in its alkyl moiety to obtain a 1-hydroxyalkyl-2-long chain alkylimidazoline, which is then reacted with a monohalogenated lower carboxylic acid having an alkylene or hydroxyl-substituted alkylene group containing from 1 to 4 carbon atoms or its salt with sodium, potassium, NH$_4$ or an alkanolamine in the same manner as for the reaction between a tertiary amine and a monohalogenated acetate in the synthesis of the compounds of formula (II).

Specific examples of the imidazoline compounds of formula (III) are shown below:

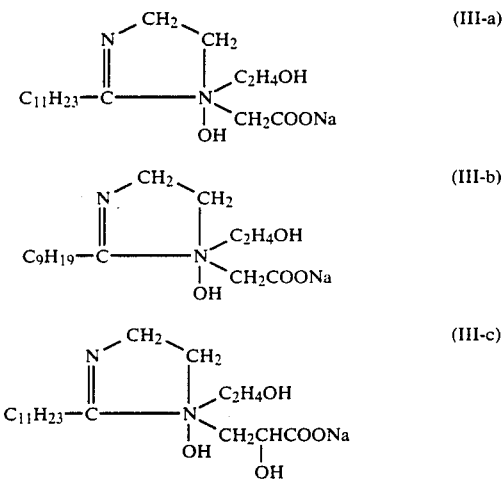

In the liquid detergent composition according to the present invention, the ratio of the N-acylaspartic acid or a salt thereof to the N-containing surface active agent is not particularly limited, and a synergistic effect can be produced as long as these two components are used in combination. Particularly excellent performance properties can be assured with a weight ratio of the N-acylaspartic acid or a salt thereof to the N-containing surface active agent falling within a range of from 1:5 to 5:1. The imidazoline compounds of formula (III) are preferred to the compounds of formula (II) to be combined with the N-acylaspartic acid or a salt thereof.

The detergent composition according to the present invention is mild to the skin, has excellent foamability even in the presence of oily dirt, and exhibits excellent detergency for heavy oily dirt.

If desired, the detergent composition of the present invention may further contain commonly employed adjuncts, diluents, thickeners and builders, such as hydrotrops, flavors, dyes, fluorescent dyes, and organic or inorganic builders.

The present invention is now illustrated in greater detail by way of the following Examples, but it should be understood that the present invention is not deemed to be limited thereto.

EXAMPLE 1

A liquid detergent composition containing sodium N-lauroyl-L-aspartate and lauryldimethylaminoacetic acid betain in proportions shown in Table 1 was prepared. The resulting detergent was evaluated for foamability, detergency and mildness to the skin according to the following test methods. The results obtained are shown in Table 1.

(1) Foamability

The detergent was 200-fold diluted with distilled water. A 20 ml portion of the thus diluted detergent was put in a 100 ml-volume measuring cylinder with a ground-glass stopper together with 1 g of triolein as an oil component. The cylinder was stoppered and given 20 vertical sharp shakings. Immediately after the shaking, the stopper was removed, the cylinder was placed horizontally, and the volume of the foam was read out.

(2) Detergency

Slide glass was dipped in a model dirt having the following composition for 1 to 2 seconds and then air-dried. The slide glass having adhered thereto the dirt was washed with the liquid detergent composition 200-fold diluted with distilled water (content of surface active agent: 0.1% by weight) at 25° C. for 3 minutes under rotation of 250 rpm and then rinsed with distilled water at 25° C. for 1 minute by means of a Leenerts improved detergency testing machine. The slide glass was air-dirted, and the residual oil was determined. A detergency (%) can be calculated from equation:

$$\text{Detergency (\%)} = \frac{W_s - W_w}{W_s} \times 100$$

wherein Ws is the amount of the deposited oily dirt before washing; and Ww is the amount of the oily dirt remaining after washing.

| Composition of Model Dirt | |
|---|---|
| Soybean oil (JP) | 10 g |
| Beef tallow (JP) | 10 g |
| Monoolein | 0.25 g |
| Oil red | 0.1 g |
| Chloroform | 60 ml |

(3) Mildness

A ultraviolet-visible detector ("UV-8010" manufactured by Toso K.K.; detection wavelength: 220 nm) was connected to a high performance liquid chromatograph ("CCPM" manufactured by Toso K.K.), and a column ("TSK-GEL 3000XL") was fitted to the chromatograph. In a phosphoric acid buffer (pH 6.8) were dissolved 9 ml of a protein aqueous solution containing 0.025% by weight of egg yolk albumin and 1 ml of the detergent composition containing 10% by weight of the surface active agent to prepare a sample. The sample (50 μl) was passed through the column and then eluted with a phosphoric acid buffer (pH 6.8) at a flow rate of 1 ml/min. The elution peak height ($H_s$) of egg yolk albumin in the fraction collected between 11 to 12 minutes from the start of elution was measured. Then, a sample prepared in the same manner except for using 1 ml of pure water in place of the detergent composition was subjected to the same chromatography, and the peak height ($H_O$) assigned to egg yolk albumin was measured. The percent denaturation of protein was calculated from equation:

Percent Denaturation (%) = $(H_O - H_s)/H_O \times 100$

Mildness was rated from the results obtained according to the following scale.

| Percent Denaturation | Rate |
| --- | --- |
| less than 10% | excellent |
| 10 to 60% | good |
| 60 to 80% | no good |
| more than 80% | poor |

COMPARATIVE EXAMPLE 1

A liquid detergent composition containing sodium N-lauroyl-L-aspartate or lauryldimethylaminoacetic acid betaine in a proportion shown in Table 1 was prepared. The properties of the resulting detergent were evaluated in the same manner as in Example 1, and the results obtained are shown in Table 1.

COMPARATIVE EXAMPLE 2

A liquid detergent composition was prepared in the same manner as in Example 1, except for using sodium N-lauroyl-L-glutamate in place of sodium N-lauroyl-L-asparate in a proportion shown in Table 1. The resulting detergent was evaluated in the same manner as in Example 1, and the results obtained are shown in Table 1.

COMPARATIVE EXAMPLE 3

A liquid detergent composition containing sodium N-lauroyl-L-aspartate or coconut oil fatty acid amidopropyldimethylaminoacetic acid betaine in a proportion shown in Table 2 was prepared. The resulting detergent was evaluated in the same manner as in Example 1, and the results obtained are shown in Table 2.

COMPARATIVE EXAMPLE 4

A liquid detergent composition was prepared in the same manner as in Example 2, except for using sodium N-lauroyl-L-glutaminate in place of sodium N-lauroyl-L-asparate in a proportion shown in Table 2. The resulting detergent was evaluated in the same manner as in Example 1, and the results obtained are shown in Table 2.

TABLE 2

| | Example 2 | | | Comparative Example 3 | | Comparative Example 4 | | |
| --- | --- | --- | --- | --- | --- | --- | --- | --- |
| Run No. | 1 | 2 | 3 | 1 | 2 | 1 | 2 | 3 |
| Composition (% by weight): | | | | | | | | |
| Sodium N-lauroyl-L-asparate | 15 | 10 | 5 | 20 | — | — | — | — |
| Sodium N-lauroyl-L-glutaminate | — | — | — | — | — | 15 | 10 | 5 |
| Coconut oil fatty acid amidopropyldimethylaminoacetic acid betaine | 5 | 10 | 15 | — | 20 | 5 | 10 | 15 |
| Ethanol | 7 | 7 | 7 | 7 | 7 | 7 | 7 | 7 |
| Urea | 3 | 3 | 3 | 3 | 3 | 3 | 3 | 3 |
| Water | balance | balance | balance | balance | balance | balance | balance | balance |
| Properties: | | | | | | | | |
| Foamability (ml) | 68 | 72 | 65 | 55 | 40 | 35 | 40 | 20 |
| Detergency (%) | 70 | 75 | 70 | 65 | 30 | 40 | 50 | 40 |
| Mildness | excellent | excellent | excellent | excellent | excellent | excellent | excellent | excellent |

EXAMPLE 2

A liquid detergent composition containing sodium N-lauroyl-L-aspartate and coconut oil fatty acid amidopropyldimethylaminoacetic acid betaine in proportions shown in Table 2 was prepared. The resulting detergent was evaluated in the same manner as in Example 1, and the results obtained are shown in Table 2.

EXAMPLE 3

A liquid detergent composition containing sodium N-lauroyl-L-aspartate and the imidazoline compound represented by formula (III-a) in proportions shown in Table 3 was prepared. The resulting detergent was evaluated in the same manner as in Example 1, and the

TABLE 1

| | Example 1 | | | Comparative Example 1 | | Comparative Example 2 | | |
| --- | --- | --- | --- | --- | --- | --- | --- | --- |
| Run No. | 1 | 2 | 3 | 1 | 2 | 1 | 2 | 3 |
| Composition (% by weight): | | | | | | | | |
| Sodium N-lauroyl-L-asparate | 15 | 10 | 5 | 20 | — | — | — | — |
| Sodium N-lauroyl-L-glutaminate | — | — | — | — | — | 15 | 10 | 5 |
| Lauryldimethylaminoacetic acid betaine | 5 | 10 | 15 | — | 20 | 5 | 10 | 15 |
| Ethanol | 7 | 7 | 7 | 7 | 7 | 7 | 7 | 7 |
| Urea | 3 | 3 | 3 | 3 | 3 | 3 | 3 | 3 |
| Water | balance | balance | balance | balance | balance | balance | balance | balance |
| Properties: | | | | | | | | |
| Foamability (ml) | 72 | 78 | 68 | 55 | 40 | 60 | 65 | 55 |
| Detergency (%) | 80 | 87 | 65 | 65 | 20 | 60 | 70 | 50 |
| Mildness | excellent | excellent | excellent | excellent | good | excellent | excellent | excellent | results obtained are shown in Table 3.

COMPARATIVE EXAMPLE 5

A liquid detergent composition was prepared in the same manner as in Example 3, except for using either one of sodium N-lauroyl-L-aspartate and the imidazoline compound. The resulting detergent was evaluated in the same manner as in Example 1, and the results obtained are shown in Table 3.

COMPARATIVE EXAMPLE 6

A liquid detergent composition was prepared in the same manner as in Example 3, except for replacing sodium N-lauroyl L-aspartate with sodium N-lauroyl-L-glutamate. The resulting detergent was evaluated in the same manner as in Example 1, and the results obtained are shown in Table 3.

TABLE 3

| Run No. | Example 3 | | | Comparative Example 5 | | Comparative Example 6 | | |
|---|---|---|---|---|---|---|---|---|
| | 1 | 2 | 3 | 1 | 2 | 1 | 2 | 3 |
| Composition (% by weight): | | | | | | | | |
| Sodium N-lauroyl-L-asparate | 15 | 10 | 5 | 20 | — | — | — | — |
| Sodium N-lauroyl-L-glutaminate | — | — | — | — | — | 15 | 10 | 5 |
| Imidazoline compound | 5 | 10 | 15 | — | 20 | 5 | 10 | 15 |
| Ethanol | 7 | 7 | 7 | 7 | 7 | 7 | 7 | 7 |
| Urea | 3 | 3 | 3 | 3 | 3 | 3 | 3 | 3 |
| Distilled water | 70 | 70 | 70 | 70 | 70 | 70 | 70 | 70 |
| Properties: | | | | | | | | |
| Foamability (ml) | 100 | 100 | 80 | 20 | 50 | 45 | 40 | 45 |
| Detergency (%) | 95 | 95 | 85 | 30 | 40 | 50 | 50 | 60 |
| Mildness | excellent | excellent | excellent | excellent | excellent | excellent | excellent | excellent |

While the invention has been described in detail and with reference to specific embodiments thereof, it will be apparent to one skilled in the art that various changes and modifications can be made therein without departing from the spirit and scope thereof.

What is claimed is:

1. An aqueous liquid detergent composition containing a detergent effective amount of a surfactant mixture containing and N-acylaspartic acid or a salt thereof selected from the group consisting of N-lauroylaspartic acid, N-myristoylaspartic acid, N-palmitoylaspartic acid, N-stearoylaspartic acid, N-palmitoylaspartic acid, N-oleoylaspartic acid or N-cocoylaspartic acid and a nitrogen-containing surface active agent selected from the group consisting of an alkylbetaine or an alkylamidobetaine represented by formula (II):

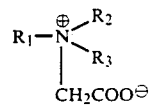

where in $R_1$ is lauryl or cocoamido and $R_2$ and $R_3$ each represents an alkyl group having from 1 to 3 carbon atoms, and an imidazoline compound represented by formula (II):

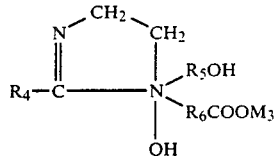

wherein $R_4$ represents an alkyl or alkenyl group having from about 9 to about 11 carbon atoms; $R_5$ represents an alkylene group having from 1 to 4 carbon atoms; $R_6$ represents an alkylene group having from 1 to 4 carbon atoms or a hydroxy-substituted alkylene group having from 1 to 4 carbon atoms; and $M_3$ represents a hydrogen atom or a cation derived from Na, K, $NH_4$ or an alkanolamine, the weight ratio of said N-acylaspartic acid or salt thereof to said N-containing surface active agent ranging from about 1:3 to 3:1.

2. A liquid detergent composition as claimed in claim 1, wherein said nitrogen-containing surface active agent is the imidazoline compound.

* * * * *